(12) United States Patent
Racca et al.

(10) Patent No.: US 7,189,970 B2
(45) Date of Patent: Mar. 13, 2007

(54) IMAGING OF FUGITIVE GAS LEAKS

(75) Inventors: Roberto Racca, Victoria (CA); James Ivor Symons, New Westminster (CA)

(73) Assignee: Power Diagnostic Technologies Ltd., New Westminster (CA)

( * ) Notice: Subject to any disclaimer, the term of this patent is extended or adjusted under 35 U.S.C. 154(b) by 93 days.

(21) Appl. No.: 10/927,122

(22) Filed: Aug. 27, 2004

(65) Prior Publication Data

US 2005/0156111 A1 Jul. 21, 2005

Related U.S. Application Data

(60) Provisional application No. 60/498,665, filed on Aug. 29, 2003, provisional application No. 60/562,989, filed on Apr. 19, 2004.

(51) Int. Cl.
*G01N 21/00* (2006.01)

(52) U.S. Cl. .................................................. 250/338.5

(58) Field of Classification Search .............. 250/338.5
See application file for complete search history.

(56) References Cited

U.S. PATENT DOCUMENTS 5,258,618 A * 11/1993 Noble ........................ 250/332
5,373,160 A * 12/1994 Taylor ...................... 250/338.5
5,656,813 A * 8/1997 Moore et al. ............... 250/330

* cited by examiner

*Primary Examiner*—Constantine Hannaher
(74) *Attorney, Agent, or Firm*—Freedman & Associates

(57) ABSTRACT

The invention relates to an imager system for imaging of a plume of a fugitive gas, dependent upon an electromagnetic wavelength absorption characteristic of the gas. A bi-spectral selector assembly houses first and second filters in separate first and second optical paths for transmittal of electromagnetic energies emanating from the scene of interest. The first and second filters have adjacent mutually exclusive narrow band pass characteristics only one of which corresponds to the electromagnetic wavelength absorption characteristic of the gas. An imager captures first and second image data having traversed the first and second filters in a frame which is then processed by correlating the image data to provide displayable data including an indication of any plume of the fugitive gas. The data is displayed in real time. In one example a CCD video camera provides picture data which is displayed with the image of the plume of gas pasted thereupon.

18 Claims, 11 Drawing Sheets

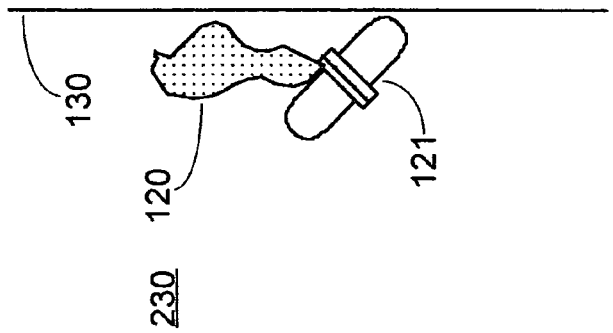
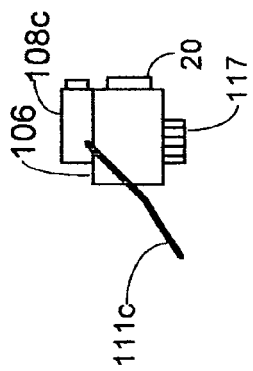
Fig. 1a
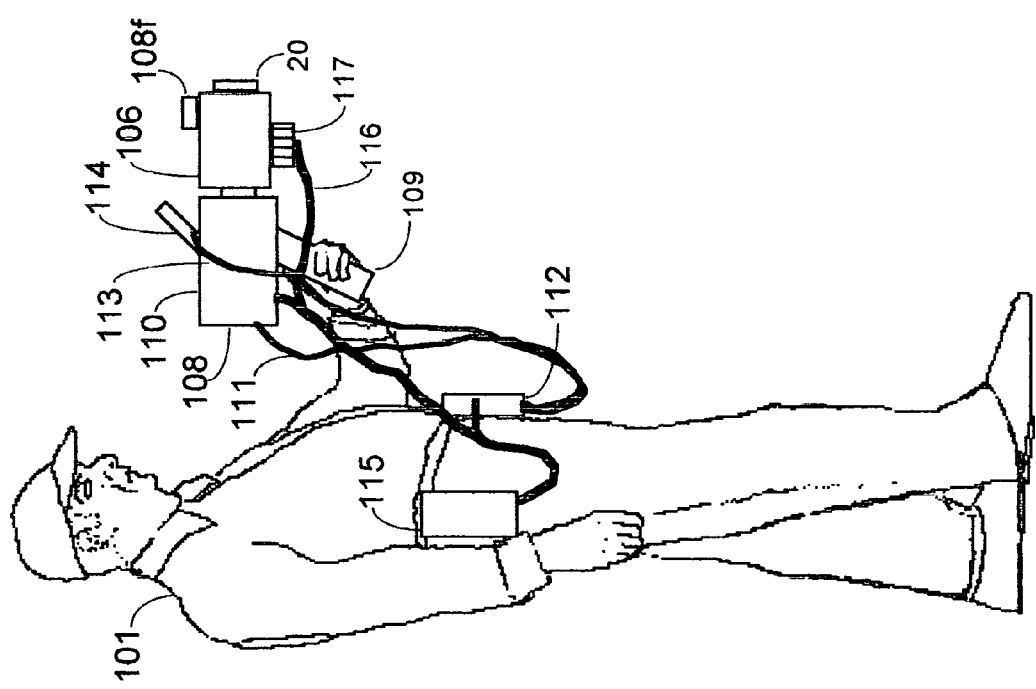
Fig. 1

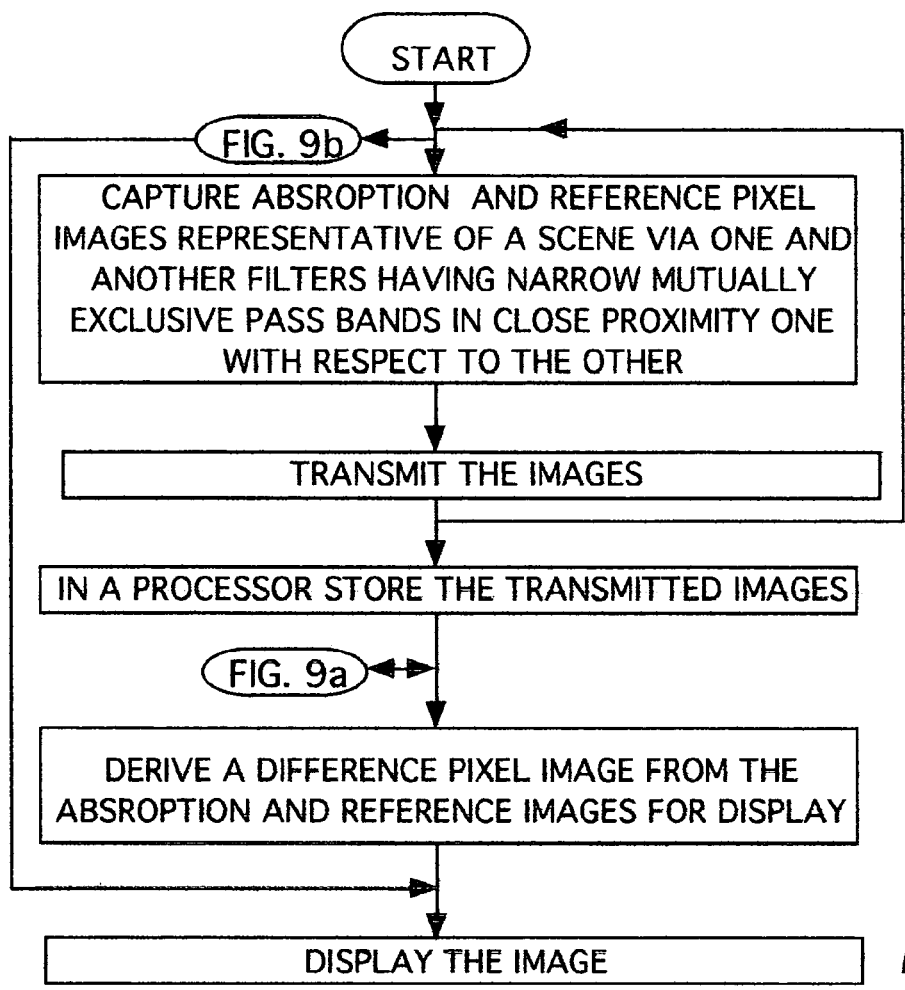

IMAGING OF FUGITIVE GAS LEAKS

This application claims benefit from U.S. Provisional Application No. 60/498,665 filed Aug. 29, 2003, and U.S. Provisional Application No. 60/562,989 filed Apr. 19, 2004.

FIELD OF THE INVENTION

The present invention relates to remote detection and imaging of gas leaks based upon electromagnetic absorption and emission characteristics of a gas of interest, using optical techniques and image processing for localization a gas leak.

BACKGROUND OF THE INVENTION

It is of great interest to be able to detect and image leakage of widely used industrial gases such as, for example, sulphur hexafloride gas (SF6) and gaseous hydrocarbons. For example small but cumulatively significant releases of methane, as from oil rigs, tank farms, pipelines and compression stations constitute an economical loss for petrochemical industries, an environmental problem and a safety concern. Releases in connection with accidents involving transport vehicles or in industrial operations and land fill garbage dump sites need to be identified. In the electrical energy generation and distribution industries, pressurized SF6 gas is widely relied upon as an insulating coolant in electrical apparatus including power transformers. Leakage is a random but chronic problem. If an overheating problem is undetected expensive equipment failure may follow, and if detected, at least the coolant needs replenishing. A minor leak may discharge only a fraction of a gram per minute and hence is difficult to detect and localize. Over a period of a few years such minor leakage may add up to many tens or even hundreds of kilograms, necessitating the expense of replacement SF6 gas and the time of skilled technicians in maintenance activities that may have otherwise been avoidable if the leakage was readily identifiable and hence remedied. Among the physical characteristics of most gases are those of line spectral absorbtion and emission of electromagnetic energy. Most gases are unique in this characteristic, as with respect to other gases. In other words a gas will exhibit an absorption of energy of a particular wavelength, or possibly of several different wavelengths, somewhere within in a spectrum of a range of deep infrared though high ultra violet, while energies of other wavelengths pass through the gas unimpeded. For example, SF6 exhibits an intense absorption characteristic at 10.6 micrometers. Methane exhibits an intense absorption characteristic at 7.7 micrometers and a less intense but significant absorption characteristic at 3.2 micrometers. Gas imaging is performed based on the wavelength absorption characteristic of a gas of interest in the electromagnetic spectrum including ultraviolet through infrared. Active gas imaging techniques use an artificial light source such as a scanning laser, tuned to the absorption wavelength of the gas, in contrast with passive gas imaging techniques which use natural light and background electromagnetic radiation. It is, therefore, desirable to image and localize a fugitive gas leakage by using a portable apparatus which is functional, while an operator of the apparatus is somewhat remote from the source of the leak. A portable and economical imaging device would expedited appropriate repair of apparatus showing gas leaks.

Active gas imaging tends to be cumbersome and expensive. One example of an active gas imaging technique is disclosed by McRae et al. in U.S. Pat. No. 4,555,627, issued on Nov. 26, 1985. McRae et al. disclose a video imaging system for detecting gas leaks. Visual displays of invisible gas clouds are produced by radiation augmentation of the field of view of an imaging device by radiation corresponding to an absorption line of the gas to be detected. The field of view of an imager is irradiated by a scanning laser beam. When a detectable gas is present, back-scattered laser beam is highly attenuated, producing an image with a region of contrast.

Passive gas imaging although less expensive than active gas imaging tends to be less sensitive. An example is disclosed in U.S. Patent Application 20030025081 filed Feb. 6, 2003, to Edner et al. wherein a passive gas imaging technique is disclosed. Edner et al. teach a method for imaging of gas emissions utilizing optical techniques combining gas correlation techniques with thermal background radiation or self-emission radiation. A simultaneous recording of images with and without filtering through a gas-filled cell is utilized for the identification of a selected gas.

Both gas imaging techniques have substantial drawbacks and performance limits. The active gas imaging techniques requires a laser source and complex associated equipment which limits their applications in the field where portability is required. The passive gas imaging technique employs a gas cell within a cumbersome optical array and is generally less sensitive. Both techniques tend to be limited to operation in relatively close proximity to the suspected gas leak and detection of only higher volumes of gas.

SUMMARY OF THE INVENTION

In accordance with an aspect of the invention, a gas imaging system for imaging a scene of interest, which may include a plume of a predetermined gas, includes a bi-spectral selector assembly for providing separate first and second paths for transmittal of electromagnetic energies emanating from the scene of interest; a first narrow band pass filter in the first path for passing electromagnetic energy of a first wavelength corresponding to an electromagnetic wavelength absorption characteristic of the predetermined gas to the substantial exclusion of other electromagnetic energy; a second narrow band pass filter in the second path for passing electromagnetic energy of a second wavelength in proximity of the first wavelength and to the substantial exclusion of electromagnetic energy of the first wavelength; an imager for capturing first and second image data of the scene of interest as represented by electromagnetic energies having traversed the first and second narrow band pass filters respectively, and, a processor in data communication with the imager for processing the first and the second image data, and in dependence thereupon providing displayable data including an indication of the presence of a plume of the predetermined gas.

Further in accordance with this aspect of the invention first and second image data are captured by the imager as first and second pixel data in a frame for transmission to the processor, after transmission of the frame the imager subsequently captures another first and second pixel data in an other frame for transmission to the processor, and so on, whereby said frames of pixel data are representative of successive real time images of the scene of interest.

In accordance with an other aspect of the invention, a gas imaging system for detecting a fugitive gas includes a first filter for filtering received image radiation indicative of a scene which may include a plume of the fugitive gas, such that only spectral components of the radiation in a narrow wavelength band centred at an absorption wavelength of the gas are passed; a second filter for filtering received image radiation indicative of the scene, such that only spectral components of the radiation are passed in a narrow wavelength band centred in proximity of the absorption wavelength of the gas to the substantially exclusion of electromagnetic energy of the absorption wavelength of the gas; a first imager in optical communication with the first filter for sensing the first image radiation and for providing first image data in dependence thereupon; a second imager in optical communication with the second filter for sensing the second image radiation and for providing second image data in dependence thereupon; and, a processor for correlating the first and the second image data and providing data indicative of an image of the plume of the fugitive gas.

In accordance with a further aspect of the present invention, a gas imaging system for detecting a fugitive gas includes; a first filter for filtering received image radiation indicative of a scene comprising a plume of the fugitive gas such that only spectral components of the radiation in a narrow infrared wavelength band centred at an absorption wavelength of the gas are passed; a second filter for filtering the received image radiation such that only spectral components of the radiation in a narrow wavelength band in proximity of the absorption wavelength of the gas are passed; an infrared imager in optical communication with the first and the second filters comprising a first portion of a sensor array for receiving and sensing the first image radiation and a second portion of a sensor array for receiving and sensing the second image radiation; the first and second portions providing first and second image data respectively; and, a processor in data communication with the infrared imager for correlating the first and the second image data and for providing data indicative of an image indicative of the plume of the fugitive gas in dependence thereupon.

In accordance with yet a further aspect of the present invention, a method for detecting a fugitive gas includes the steps of: receiving image radiation indicative of a scene comprising a plume of the fugitive gas; filtering a first portion of the received image radiation such that only spectral components of the radiation in a narrow wavelength band centred at an absorption wavelength of the gas are passed; filtering a second portion of the received image radiation such that only spectral components of the radiation in a narrow wavelength band centred in proximity of the absorption wavelength of the gas are passed; sensing the first image radiation and the second image radiation and providing first and second image data, respectively; correlating the first and the second image data; and, generating an image of the fugitive gas plume in dependence upon the correlated first and second image data.

In one example the method includes the further steps of receiving a visable spectrum image of the scene and correlating the image of the fugitive gas plume with the visable image whereby in a visual display of a composite frame, a significant plume of the fugitive gas is identifiable and localized within the scene.

In accordance with yet a further aspect of the present invention, a method for imaging a scene in which there may be a plume of a fugitive gas of interest includes the steps of:

m) capturing first and second pixel image data representative of the scene via first and second filters having narrow mutually exclusive pass bands in close proximity one with respect to the other, the pass band of the first filter being centred on a wavelength corresponding to an absorption wavelength of the gas of interest;

n) transmitting the first and second pixel image data to a processor; and o) deriving a difference pixel image partial frame by a subtraction of a fractional area of second the pixel image data from a corresponding fractional area the first pixel image data; and, p) correlating the difference pixel image partial frame with either the second pixel image data and a visable spectrum pixel image data representative of the scene to generate a composite frame;

whereby in a visual display of the composite frame a significant plume of the fugitive gas is identifiable and localized with respect to the scene.

In one example of the invention the bi-spectral selector assembly is contained within a vessel having an interior cavity being defined by end walls being spaced one from an other and a side wall extending between and connected with the end walls, each end wall including an optical port, one of the optical ports for receiving electromagnetic energies emanating from the scene of interest and the other of the optical ports for coupling any electromagnetic energies having traversed the first and second narrow band filters to the imager, and a sun shade comprising an auxiliary wall spaced adjacent a portion of the side wall, whereby in normal use at least the side wall of the vessel is substantially shaded from any incident sunlight.

In a second example of the invention the a bi-spectral selector assembly is contained within a vessel having an interior being defined by end walls being spaced one from an other and a side wall extending between and connected with the end walls, each end wall including an optical port, one of the optical ports for receiving electromagnetic energies emanating from the scene of interest and the other of the optical ports for coupling any electromagnetic energies having traversed the first and second narrow band filters to the imager, and the vessel further includes a thermal impedance material extending along surfaces of the walls the cavity.

In an other example, the gas imaging system includes a heat transfer element external of the cavity and in thermal contact with at least the narrow band pass filters, whereby the cavity is maintained cooler than the ambient atmosphere

BRIEF DESCRIPTION OF THE DRAWINGS

Exemplary embodiments of the invention are described in conjunction with the accompanying drawings in which:

FIG. 1 is a simplified sketch of a gas imaging system depicted in a typical use situation, in accordance with the invention, and FIG. 1a shows a preferred variation wherein a CCD video camera is used in conjunction with the gas imaging system;

FIGS. 9, 9a and 9b are each a flow diagram representation illustrating methods of operation of the gas imaging system in accordance with the invention;

DESCRIPTION

Figure 2:
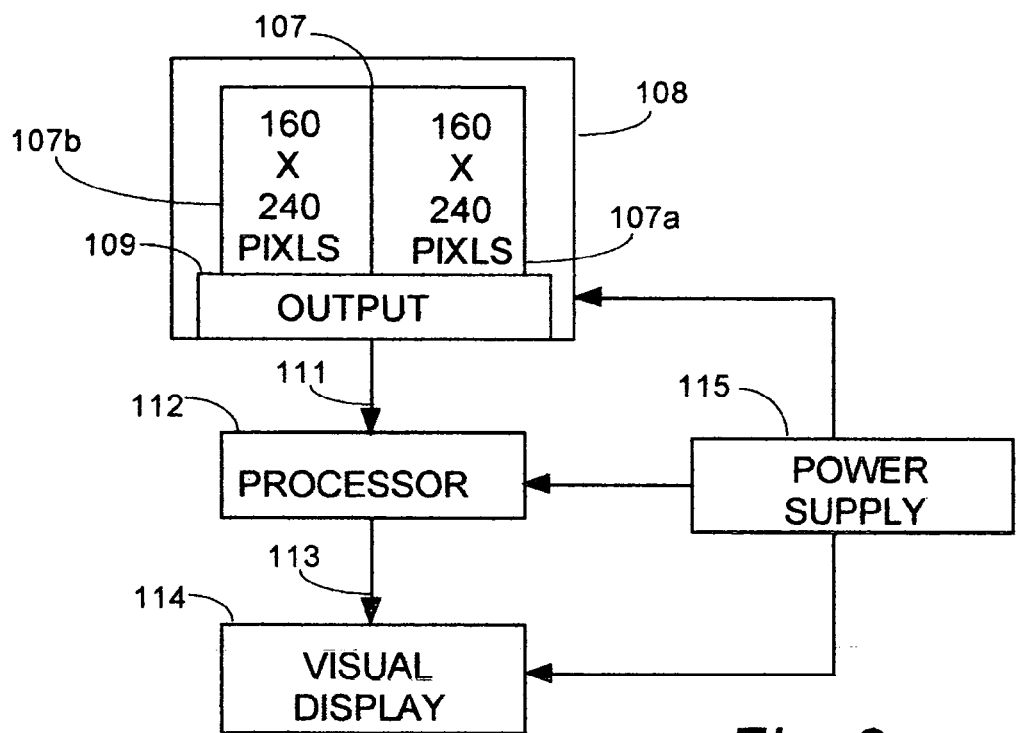
FIGS. 2, 2a and 2b are block schematic diagrams of part of the gas imaging system depicted in FIG. 1.

A gas imaging technique, as described herein, is based on differential narrow band absorption in Mid- or Long-Wavelength IR of either back scattered active lighting, thermal background radiation or a combination of both. The absorption in the Mid- or Long-Wavelength IR is useful for detecting gas leaks of methane and SF6. It has been realized that images of identical scan, captured by wavelength narrow pass band filters with pass bands that are in close proximity are substantially identical unless a substance which absorbs or emits in only one of the pass bands is in the scene. Such a substance is readily detectable as only the substance is responsible for comparative differences of electromagnetic energies representing images of the scene.

Referring to FIG. 1, a gas imaging system generally at 100 is illustrated in a typical use at a scene 230 which is of interest. The scene 230 includes a background shown generally at 130, a flanged conduit 121 and a plume of fugitive gas 120, escaping from the flanged conduit 121 and dissipating in the atmosphere. A gas imaging device 110 is hand held via a handle 109, by an operator come observer 101 the gas imaging device 110 includes a bi-spectral selector 106 coupled with an infrared (IR) imager 108. In this example a cooling device 117 is incorporated with the bi-spectral selector 106 for reducing background thermal noise and thereby improving sensitivity. A Peltier cooling device, sometime referred to as a TE cooler, has been found useful. The scene 230 is viewed by the IR imager 108 through the bi-spectral selector 106 via a port or window 20. The IR imager 108 is coupled via a transmission cable 111 to transmit video images in Firewire format to a processor 112. In operation the video images are processed in real time, to produce an image showing the gas plume 120 being localized against the background 130 of the scene 230. In this example the image is transmitted via a transmission cable 113 to a display 114 mounted on the imager 108, for viewing by the observer 101. The IR imager 108, the processor 112 and the Peltier cooling device 117 are shown to be connected to a battery pack 115 via a power cable 116, whereby hours of portable operation are available. In FIG. 1 a flash source 108f synchronized with the camera 108 is shown carried by the bi-spectral selector 106.

Figure 2A:
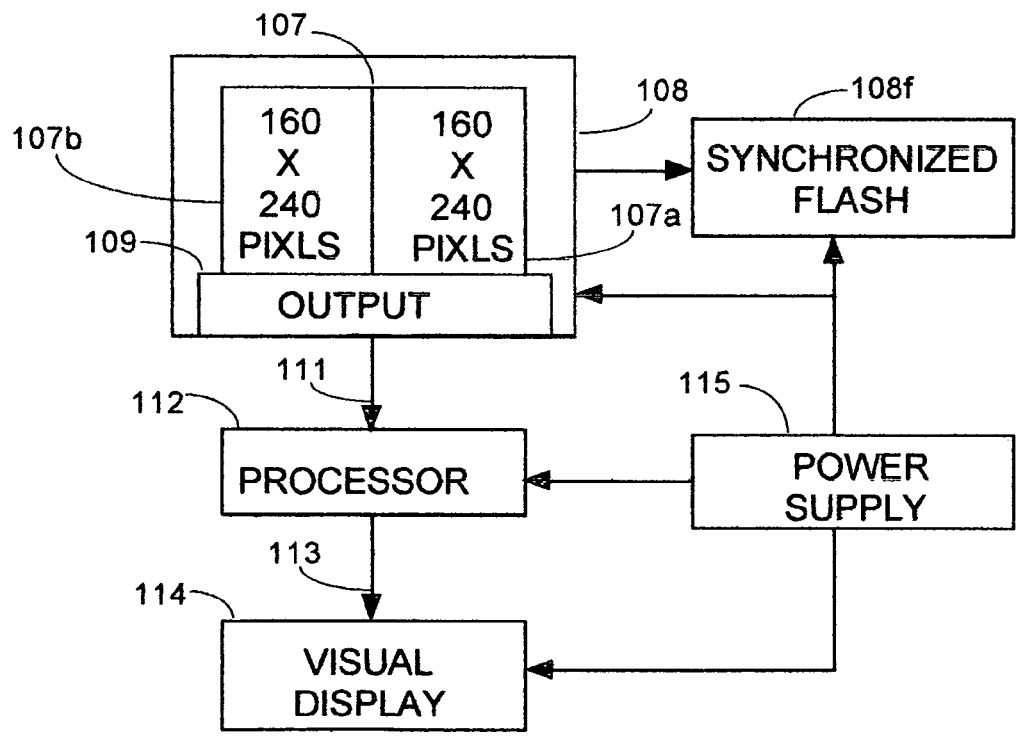
Figure 2B:
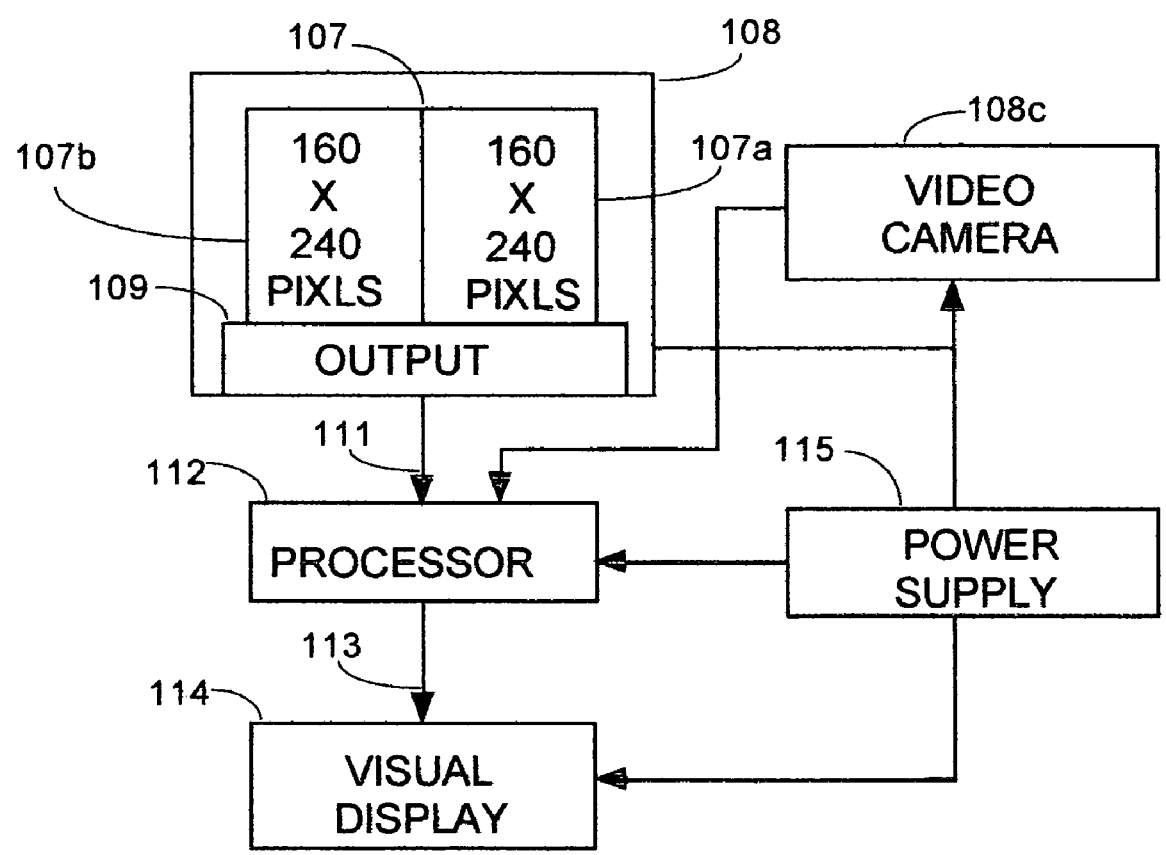

Referring to FIG. 2, the IR imager 108 in this example is an infrared microbolometer, available under the trademark Mikron 7200. The IR imager 108 includes an image array 107 which has at least 320 pixels horizontally and 240 pixels vertically. When the IR imager 108 is coupled with the by-spectral selector 106, halves 107a and 107b are separately illuminated by the scene to produce image data for each of 160×240 pixels. The Mikron 7200 operates to produce image frames at a rate sufficient for real time video display with each frame being normalized in contrast and brightness. An output buffer delivers frame organised pixel data via the cable 111 to the processor 122, in accordance with a transmission standard known as Firewire. Any convenient microprocessor may be used. In this example a PROTEUS P4 microprocessor, adapted for portable use by Interay BV of the Netherlands is used. After performing correlating and processing functions upon each frame, the processor 112 provides a composite NTSC video signal to the display 114. In this example the display 114 is part of the Mikron camera. A batter pack 115, carried by the operator, powers the processor 112 as shown in FIG. 1. It is possible that a more suitably economical camera other than the Mikron 7200 may be used to provide the IR imager 108. As such it is envisaged that the task of normalizing the images will be performed in the processor 112 separately and thus be optimizable to contribute to improving functional sensitivity of the imaging system. If the different camera lacks a display an auxiliary TFT LCD display available from Purdy Electronics of California is thought to be satisfactozy. In FIG. 2a the infrared flash 108f is shown couple to the camera 108 for synchronized operation with the camera and coupled to the power supply in order to receive energizing current. In FIG. 2b a video camera 108c provides a visible spectrum image over which the image 120 is registered so that the location of any detected plume will be more conveniently apparent to the operator 101.

Figure 3:
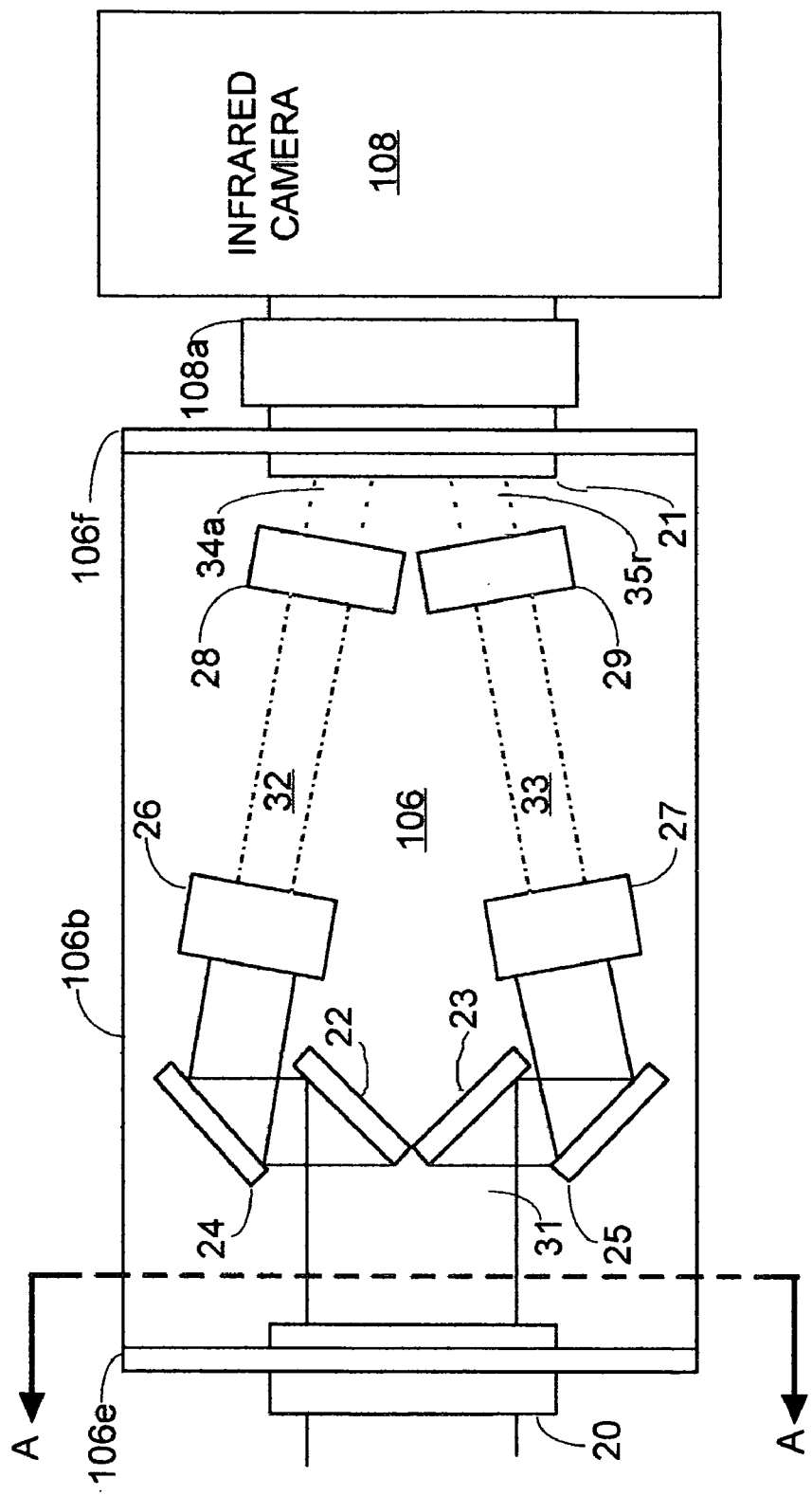
FIG. 3 is a plan view diagram of a bi-spectral selector assembly in combination with an infrared camera in the gas imaging system as depicted in FIG. 1.

Referring to FIG. 3, the bi-spectral separator assembly 106 is shown as releasably coupled by an attachment ring 108a to the infrared camera 108. The infrared camera in this example is a Mikron model 7200, also sometimes generically referred to as a microbolometer. The interior of the bi-spectral separator assembly 106 is shown in a plan view as would appear with its cover removed. The bi-spectral separator assembly 106 includes a base 106b with end portions 106e and 106f extending normal thereto. Lens structures or windows 20 and 21 are mounted in the end portions 106e and 106f, as shown. In this example the lens structure 20 is of a germanium glass 50 mm objective lens mounted in a sun shield ring. The lens structure 20 is for the ingress of electromagnetic energy, indicated as an incident beam 31. Incident mirrors 22 and 23 and directive mirrors 24 and 25, are arranged to split the electromagnetic energy 31 into two beams which are directed to infrared optical assemblies 26 and 27, respectively as shown. The infrared optical assemblies 26 and 27 function to limit the beams 34a and 35a, respectively, to rectangular cross sectional dimensions appropriate for separately illuminating the halves 107a and 107b of the array 107, shown in FIG. 2, and to collimate each of the beams, preparatory to filtering. In this example in operation electromagnetic energy is directed from the mirrors 24 and 25 through each of the infrared optical assemblies 26 and 27 where the electromagnetic energy in each beam traverses of a field stop aperture, followed by a field lens, followed by a collimating lens (said apertures and lenses not shown). Infrared electromagnetic energies having traversed the infrared optical assemblies 26 and 27 have been collimated, into beams labelled 32 and 33. The collimated beams 32 and 33 impinge upon narrow band filters 28 and 29 and any energies passing there through are referred to as absorptive and reference beams 34a and 35r respectively, which are passed via an exit window 21 mounted in the end portion 106f. The absorptive and reference beams 34a and 35r are of rectangular cross sectional dimensions appropriate for separately illuminating the halves 107a and 107b of the array 107. As this particular example of the bi-spectral separator assembly 106 is intended to operate in the infrared spectrum, the lens structures 20 and 21 include lenses or windows, not shown, of germanium glass. The mirrors 23–25 are polished aluminum plates. The absorptive and reference filters 28 and 29 are available from Barr Associates of Massachusetts.

Figure 4:
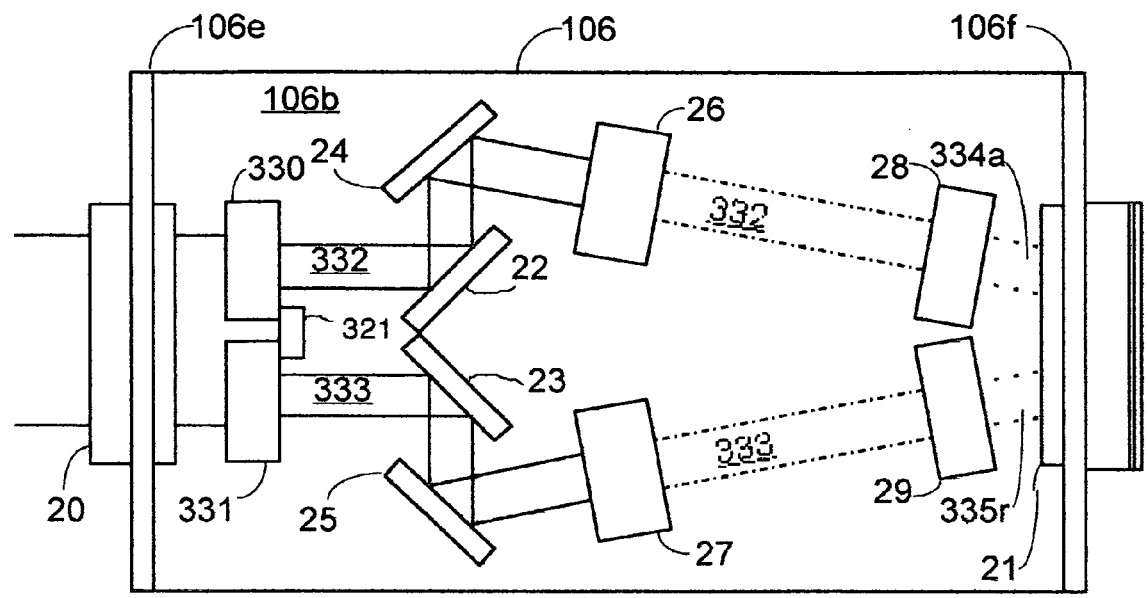
FIG. 4, is a plan view diagram of an other example of a bi-spectral selector assembly, similar to that illustrated in FIG. 3.

Referring to FIG. 4, the illustrated example of a bi-spectral selector assembly is somewhat similar to that illustrated in FIG. 3 and hence elements similar to labelled elements in FIG. 3 are identified with similar labels. In this example, aperture plates or field lenses 330 and 331 are carried by the base 106b between the lens structure 20 and the incident mirrors 22 and 23. The aperture plates 330 and 331 have apertures defined therein (not shown) for limiting any electromagnetic radiation entering via the lens structure 20 to beams at 332 and 333, which are dimensionally little more than the cross sectional dimensions appropriate for illuminating the halves 107a and 107b of the array 107, illustrated in FIG. 2. The aperture plates 330 and 331 are individually mounted upon the base 106b and are individually adjustable. A plate 321 bridges a gap between the aperture plates 330 and 331. The plates are of polished aluminum, such that in combination electromagnetic radiation not within the cross sectional area of either of the beams 332 and 333 is reflected back toward the lens structure 20. As in the example in FIG. 3, the mirrors 24 and 25 direct the beams to the infrared optical assemblies 26 and 27 and thence into beams 332 and 333 which impinge upon absorptive and reference filters 28 and 29. Any electromagnetic energies traversing the absorptive and reference filters 28 and 29 emerge as beams 334a and 335r, respectively, with cross sectional dimensions appropriate for separately illuminating the halves 107a and 107b of the array 107, illustrated in FIG. 2. In operation the example of the bi-spectral separator assembly 106 illustrated in FIG. 4 is intended to expel most of the electromagnetic energy which is outside the required cross sectional dimensions of the emergent beams 334 and 335, in contrast to the operation of the assembly illustrated in FIG. 3, wherein such energy tends to contribute to background noise and may reduce the over all operational sensitivity of the system.

Figure 5:
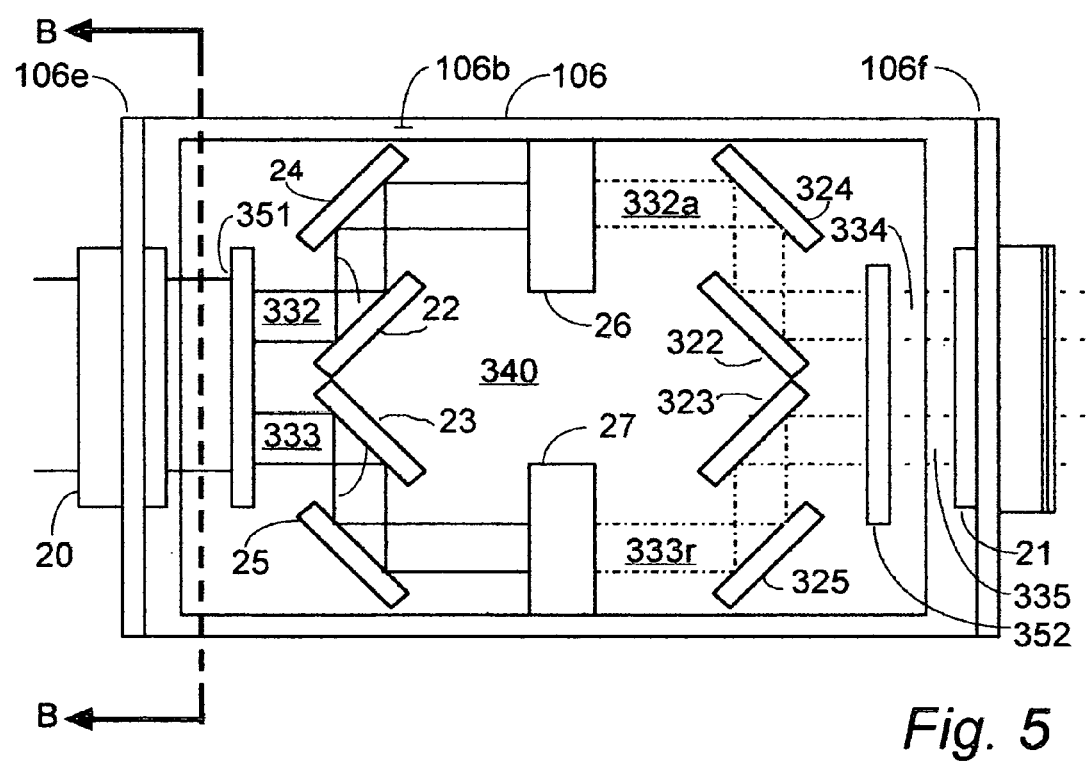
FIG. 5, is a plan view diagram of an other example of a bi-spectral selector assembly, similar to that illustrated in FIG. 3.

Referring to FIG. 5, the illustrated example of a bi-spectral selector is somewhat similar to that illustrated in either of FIGS. 3 and 4 and hence elements similar to labelled elements in FIGS. 3 and 4 are identified with similar labels in FIG. 5. In this example an internal or secondary base plate 340 carries all of the internal elements of the bi-spectral selector 106, and is in turn supported by the base 106b. The internal elements include a single aperture plate or field lens 351 for limiting the cross sectional areas of beams 332 and 333. Mirrors 22–25 direct the beams to infrared optical assemblies 26 and 27 which direct energies in beams 332 and 333 via mirrors 322–325 to an absorptive and reference filter assembly 352. Any energies traversing the filter assembly 352 emerge in beams 334 and 335, of cross sectional dimensions appropriate for separately illuminating the halves 107a and 107b of the array 107, illustrated in FIG. 2. In contrast to the structures illustrated in FIGS. 3 and 4, in this example the emergent beams are in a substantially parallel arrangement whereby a camera with separate image arrays is useful when coupled with the bi-spectral selector. On the other hand if it is required that a camera with a single image array, such as the Mikron 7200, is to be used, the mirrors 322 and 323 are mounted at appropriate angles to produce convergent beams similar to that illustrated in FIG. 3 or in FIG. 4. Likewise the filter 352 is also modified accordingly. One further advantage of the example in FIG. 5 is that in manufacture,the internal elements are preassembled upon the secondary base plate 340 and hence can be more conveniently aligned prior final assembly. Structural assemblies using a plate similar to the secondary base plate 340 are also applicable to the assemblies shown in FIGS. 4 and 3. Use of a secondary base plate is believed to provide a more robust gas imaging system, less likely to have elements becoming misaligned with time and usage.

Figure 6:
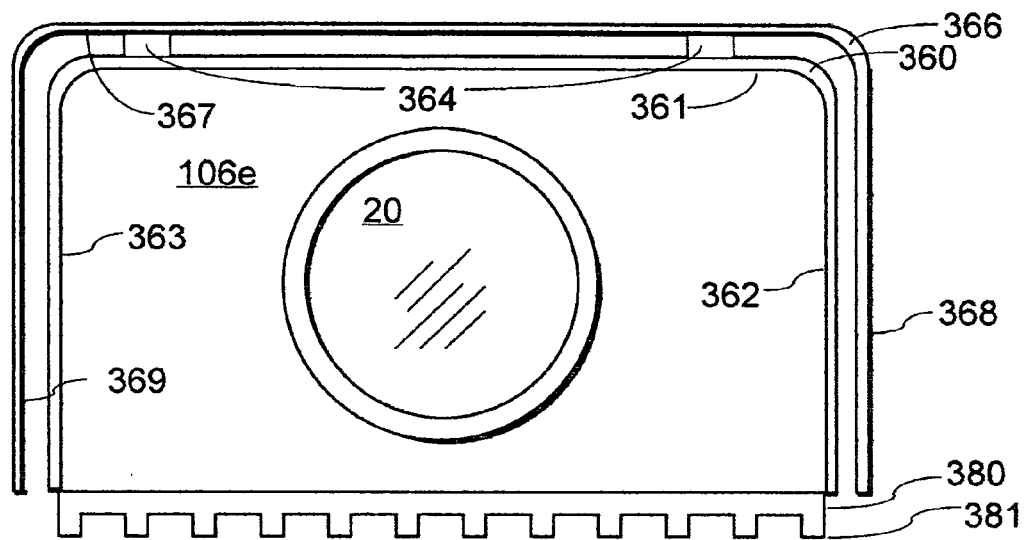
FIG. 6 is a front elevational view of one example of the bi-spectral selector assembly illustrated in FIG. 3.

Referring to FIG. 6 an example of the bi-spectral selector assembly is illustrated in elevation as it appears viewed from the left of FIG. 3. The lens assembly 20 is shown mounted in the base end portion 106e. A cover 360 includes a top portion 361 and two side portions 362 and 363 and is fixed to the base 106b, the base end portion 106e and the base end portion 106f (not visible) by any convenient fasteners (not illustrated). The cover 360 cooperates with the base 106b and the base end portions 106e and 106f to provide an enclosed cavity which contains the optical elements in a separate but not necessarily sealed environment. The environment is further isolated from outside effects by a shield 366 which includes a top portion 367 and two side portions 368 and 369. The shield is fixed in spaced relationship with the cover 360 by a four spacers 364, only two of which are visible. The shield 360 is preferably white or some light pastel shade so that electromagnetic radiation in the visible and adjacent spectrums, particularly sunlight, tends to be reflected. As the shield 360 is spaced from the cover most of any energy which may be absorbed by the shield tends to be carried off by convection with the ambient atmosphere. Also shown is a heat sink 380 fastened in thermal conductance against the base 106b. The heat sink 380 includes a series of ribs 381 for optimizing surface area interface with the ambient atmosphere. The heat sink 380 may be formed of aluminum and be fastened directly to or be integrated with the base 106b as a passive element. Alternately however, it is preferred that the heat sink 380 be provided in combination with the cooling device shown in FIG. 1, such that in operation the interior of the bi-spectral separator assembly 106 is cooled by say for example much as 10 to 15 degrees celsius. However, the interior must be maintained at a temperature warmer than the dew point of the internal atmosphere, other wise water vapour condensation will render operation unsatisfactory. In one example (not shown), the problem of condensation is avoided by perging the enclosed cavity with an inert gas from a pressurized source. For example if dry nitrogen is vented into the cavity, the ingress of the nitrogen expels the previously resident atmosphere along with any water vapour as well as cooling the cavity rapidly, after which the TE cooler can maintain a preffered operating temperature.

Figure 7:
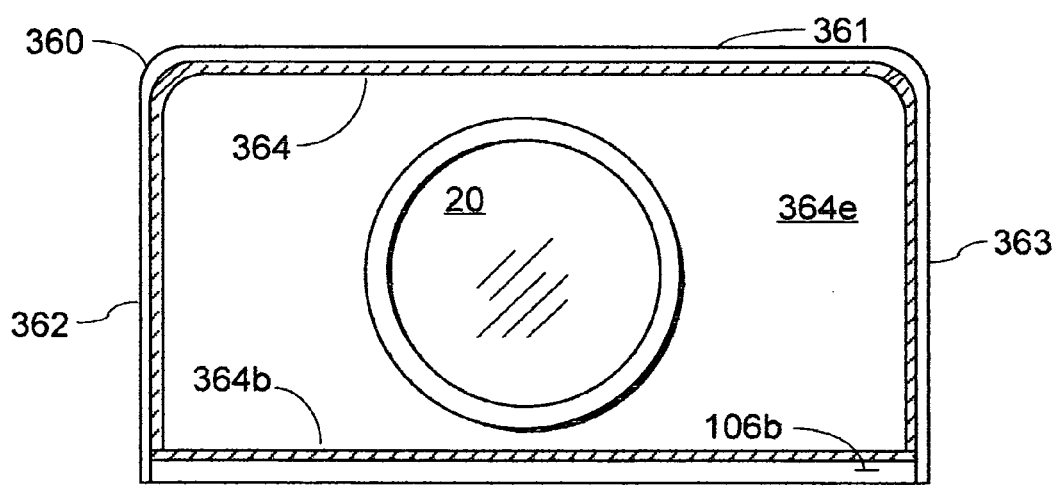
FIG. 7 is a partial sectional view of one example of the bi-spectral selector assembly illustrated in FIG. 6, taken along a line A—A in FIG. 3.

Referring to FIG. 7, an example of the bi-spectral selector assembly is illustrated in a simplified sectional elevation as it appears viewed from the right side of a line A—A in FIG. 3. In this illustration only those elements which are of assistance in understanding this particular example are shown. The base 106b and the base end portion 106e (not visible) support the cover 360. In this example the interior space of the bi-spectral separator assembly 106 is somewhat thermally isolated from the cover and the base by layers 364, 364b and 364e of insulating material carried on the interior surface of the cover 360 the interior surface of the base 106b and the interior surface of the base end portion 106e, respectively. Thus in combination with the shield 366 (not shown in this figure) the only significant heating of the interior space is from energies thermally conducted via the lens assemblies 20 and 21 and electromagnetic energies passed inwardly by the lens assembly 20 and which fails to exit via the lens assembly 21. In the simplified illustration the internal elements being mirrors, filters, and aperture plates are not shown but these elements are readily mounted upon the base by stand off fasteners so that these elements are fixed in firm spacial relationships with one another. An insulating layer of a flexible bubbled metallized mylar sheet material has been used but it is believed that a material generically referred to as aerogel would be more suitable. In an alternate example (not shown) the shield 366 and the cover 360 are integrated in a composite material of significant thermal impedance. It is envisaged for example that a medium density ridged foam material, formed in the shape of the cover 360 and with a higher density highly reflective skin, would be suitable.

Figure 8:
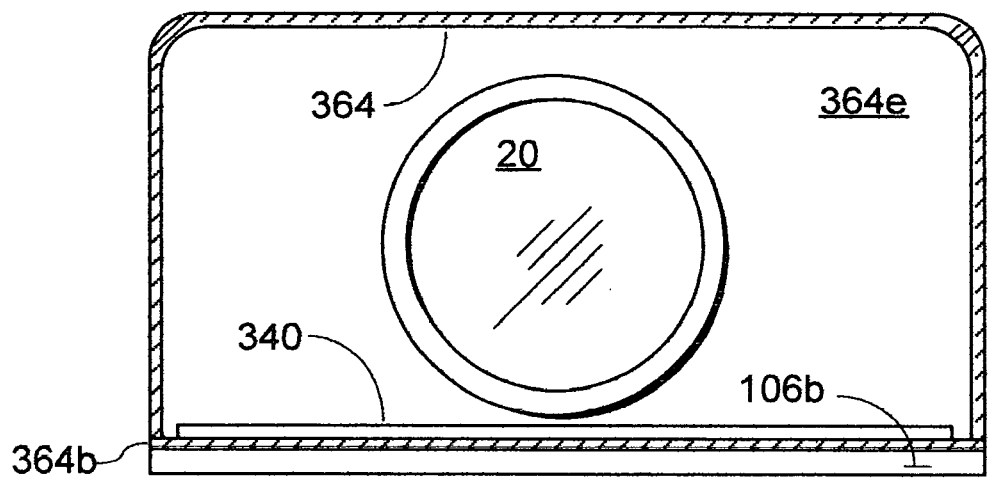
FIG. 8 is a partial sectional view of an other example of the bi-spectral selector assembly illustrated in FIG. 6, taken along a line B—B in FIG. 5.
Figure 8A:
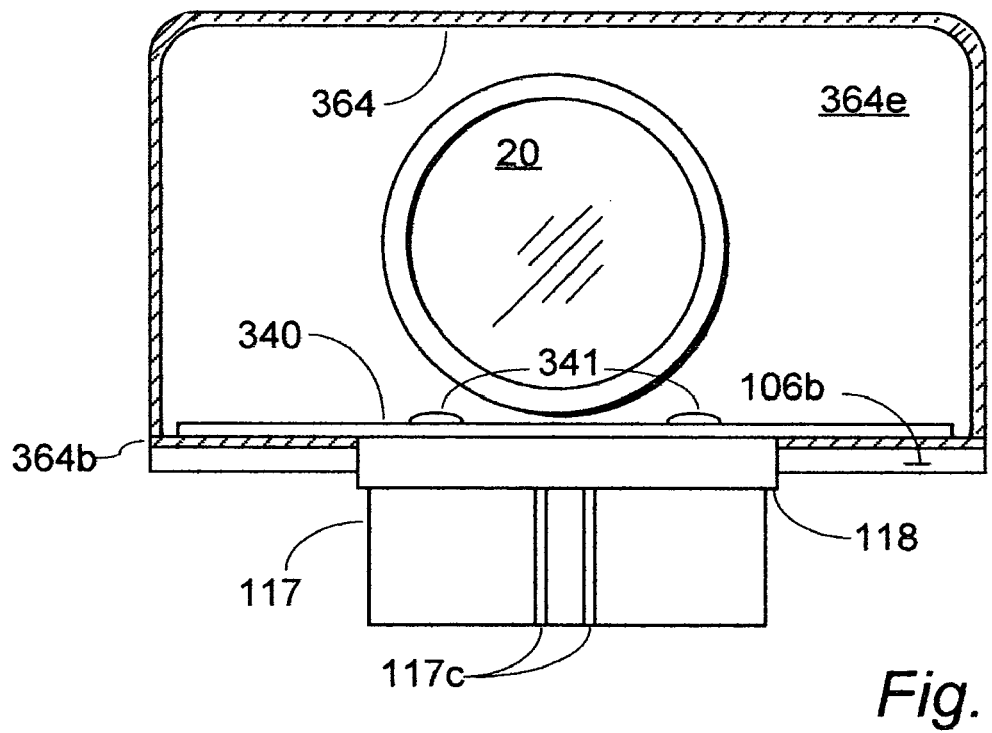
FIG. 8a is a somewhat similar view showing yet another example of the bi-spectral selector assembly.

Referring to FIG. 8, an example of the bi-spectral selector assembly is illustrated in simplified sectional elevation as it appears viewed from the right side of a line B—B in FIG. 5. The elements illustrated in FIG. 8 are similar to the elements illustrated in FIG. 7, with one exception being an internal or secondary base plate 340 which carries all of the internal elements of the bi-spectral selector 106. In this example the secondary base plate 340 is fixed to the base 106b by stand off fasteners (not visible). In FIG. 8a an other example of the bi-spectral selector assembly is illustrated in a further simplified sectional elevation similar to that in FIG. 8 however showing a section of the base plate 340 extended, toward an observer of the figure, to about the centre of the bi-spectral selector 106 to illustrate the addition of a cooling device, for example the Peltier cooler 117 shown in FIG. 1. The cooler 117 includes many heat transfer fins 117c, only two being illustrated for convenience, and is fixed in thermal communication with the secondary base plate 340 by fasteners 341. A gap in the base 106b and the layer of insulating material 364b permits the cooler 117 to be fastened directly against the secondary base plate 340, while an insulating ring thermally isolates the cooler 117 from the base 106b. Furthermore, regardless of the presents or absents of the cooler 117, the secondary base plate 340 provides a primary advantage of simplified assembly and alignment of the internal elements and a secondary advantage of maintaining the internal elements at a more or less uniform temperature.

Referring to FIG. 1 by way of reminder, the gas imaging system is illustrated in a typical use with the operator 101 viewing the scene 230. The scene 230 includes a plume of fugitive gas 120 escaping from the flanged conduit 121 and dissipating in the atmosphere. The objective of the operation of the system is to image the plume of fugitive gas 120 against the background shown generally at 130 so that the operator may view, in real time, the image displayed via the display 114 with the scene in his normal field of view and so become aware of the leakage and its precise location.

Referring to FIG. 9 one example of the operation of the gas imaging system is illustrated as a succession of functional steps. At a start of operation one and another pixel images representing a scene of interest are captured via a reference filter and an absorption filter. The absorption filter has a narrow pass band at the wavelength of absorption of a gas intended for imaging. The reference filter has a similarly narrow pass band closely adjacent the pass band of the absorption filter. Each pair of captured images are transmitted in a common raster frame of pixels, for storage by a processor and then another image is captured, and so on. The processor, for example the processor 112 in FIG. 1, optionally performs a noise reduction process upon each of raster images as shown in FIG. 9a so that any extreme pixel amplitude value in relation to immediately adjacent pixels in the raster image is normalized such that itÕs value or luminance is more adjusted to be more like the values of the immediately adjacent pixels. In any event he processor performs a pixel by pixel value subtraction of the images to derive a difference pixel image which is visibly displayed, for example as an NTSC signal prepared for viewing. In accordance with this method, a real time display of a fugitive gas emission, SF6 for example, are viewable. A preferred option is shown in FIG. 9b wherein a visible spectrum picture of the scene is captured, in real time, by the CCD video camera 108c, shown in FIG. 1a. Accordingly the picture is displayed with the image of the gas emission pasted into it. It is envisaged that greater sensitivity can be obtained when images are captured by a stationary camera in contrast to the hand held example as shown in FIG. 1, and a pixel by pixel correlation of an instant difference pixel image with a series of at least one or several preceding frames of difference pixel images is performed. It is also envisaged that by this process, if more frames are correlated this would be of an equivalent effect to the pixel noise reduction process, as noise reduction is inherent in the correlation process.

Preferably the reference filter pass band is as close as practically possible to the absorption wavelength without actually passing any significant electromagnetic energy at the absorption wavelength. For example if SF6 is of interest, ideally the centre wavelength of the pass band of the absorption filter is at about 10.6 micrometers. Narrow band filters with bass bands centred on 10.6 and 10.2 micrometers have been found to suitable. If methane is of interest, methane exhibits a strong absorption at a wavelength of 3.2 micrometers and a less strong absorption at a wavelength of 7.7 micrometers. Narrow band filters with pass bands centred on 7.7 and 8.2 micrometers have been found somewhat useful for image methane. Imaging of methane at the stronger absorption wavelength of 3.2 micrometers is quite susceptible to IR noise interference but has been demonstrated while the microbolometer is cooled or the scene is illuminated by an incandescent source rich in infrared energy. Various halide pot lamps have been found to be effective. However the use of the flash source 108f is believed to be more convenient. Such infrared flash sources are available from PerkinElmer and Phoenix Corporation, for example.

Figures 10, 10A:
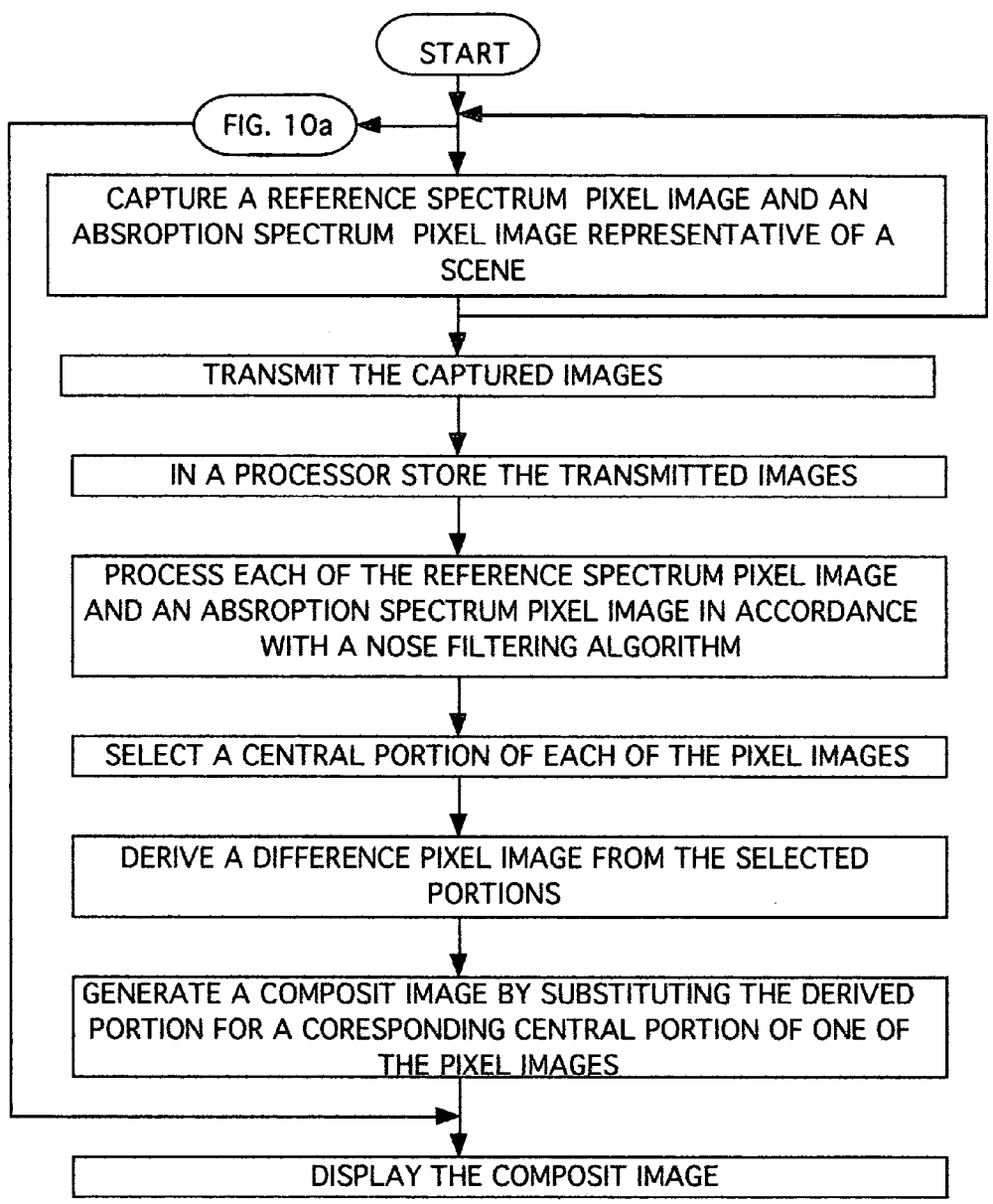
FIGS. 10 and 10a are each a flow diagram representations of variations of the method of operation illustrated in FIG. 9.

Another example of the operation of the gas imaging system is illustrated as a succession of functional steps in FIG. 10. The operation starts by capturing a pair of images, a reference spectrum pixel image and an absorption spectrum pixel image. The captured images are transmitted to a processor and then another pair of images are captured and so on. The images are stored and subsequently processed in accordance with a real time image clarifying software application, for example in IDL (Interactive Data Language) Runtime software. In this example only a central portion of each image is selected from each image from which a difference pixel image is derived. The central portion may include a fifth to a third of the whole image and reduces the number of pixels for processing while yet maintaining a periphery reference frame A composite image is derived by substituting the derived portion for the corresponding portion in one of the pair of pixel images. The resulting composite image is displayed with the advantage that a detected gas emission is imaged toward a central area of the display while being framed by a somewhat clearer visual indication of the scene immediately adjacent. A preferred option is shown in FIG. 10a wherein a visible spectrum picture of the scene is captured by the CCD video camera 108c, shown in FIG. 1a. Accordingly, the picture from the CCD video camera 108c is displayed with the image of the gas emission pasted into it.

Figure 11:
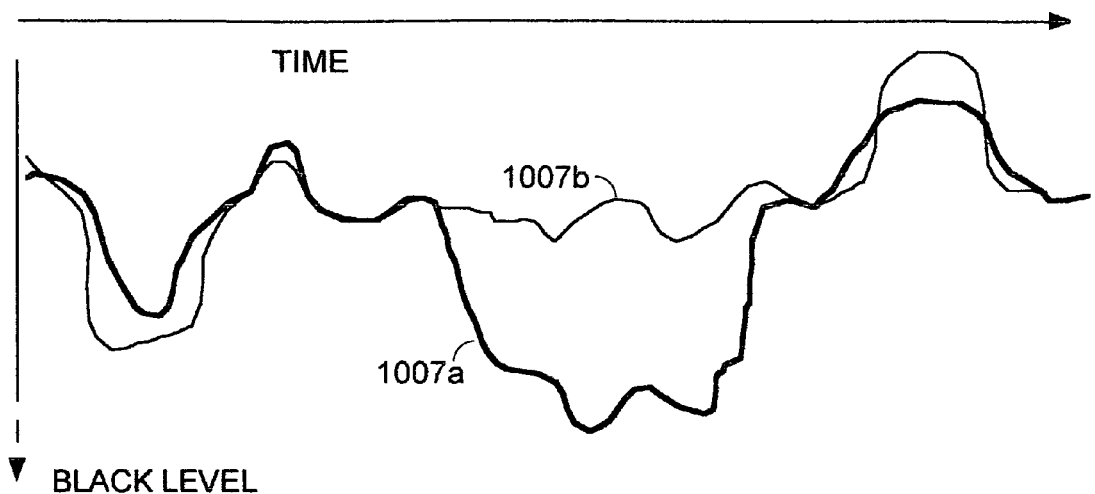
FIG. 11 is a graphical representation exemplary of absorption spectrum and reference spectrum electromagnetic energies captured by the gas imaging system as illustrated in FIGS. 1 and 2.

Referring to FIG. 11, in the graph a partial line of pixel values for an absorption spectrum image is labelled 1007a (shown as a heavy line) and a corresponding partial line of pixel values for a reference spectrum is labelled 1007b. These are exemplary of electromagnetic energies captured by the array halves 107a and 107b of the image array 107, as illustrated in FIG. 2, while the array 107 is receiving electromagnetic energies from a scene including an emission of a gas of interest. The lines are plotted against a vertical axis representing pixel values and a horizontal line representing the passage of time during which a succession of pixels from each half is transmitted from the array. The lines 1007a and 1007b are transmitted one after the other , however are illustrated in a correlated relationship for deriving a difference pixel image.

Figure 12:
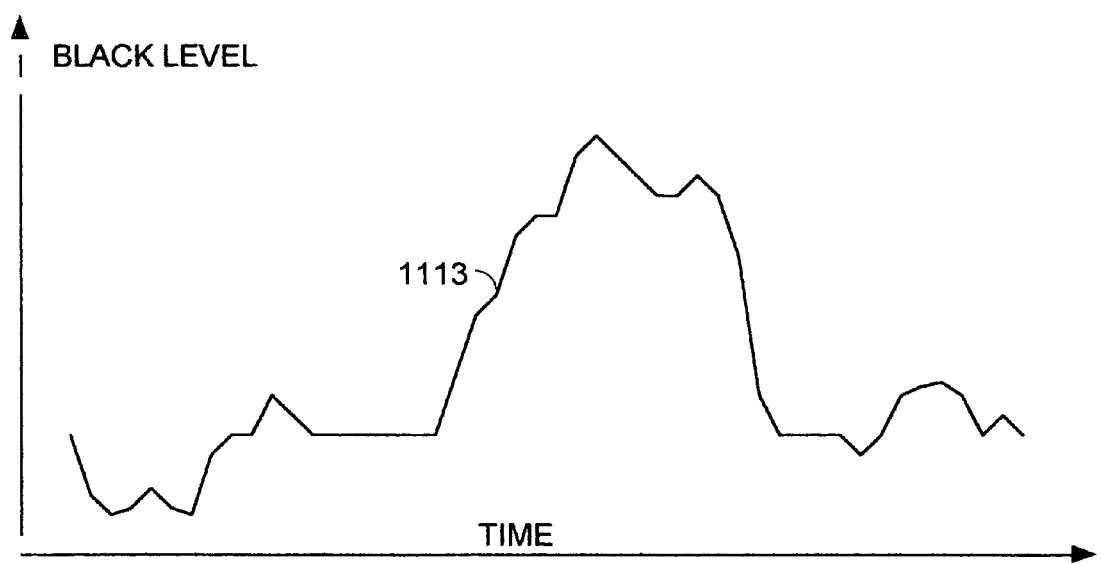
FIG. 12 is a graphical representation of image information having been derived in accordance with the invention from processing captured energies substantially as represented in FIG. 11.

Referring to FIG. 12, in the graph a line 1113 is plotted against a vertical axis representing pixel values and a horizontal line representing the passage of time. The partial line 1113 represents pixel values exemplary of that derived by a subtraction of the pixel values represented by the line 1007a from the pixel values represented by the line 1007b, in FIG. 11. The line 1113 is representative of a small fraction of the image information arranged in NTSC format and displayed for the operator by the display 114 in FIG. 1.

In a further example of imaging the scene as described in the forgoing the method includes an identification of image characteristics typical of a contiguous group of pixels in a frame which corresponding to a plume of the fugitive gas. In an event of such image characteristics being detected by the processor, the pixel locations of the group of pixels are displayed with an artificially greater contrast which may include coloration, whereby a significant plume of the fugitive gas is more readily identifiable, by an observer of the display 114.

Figure 13:
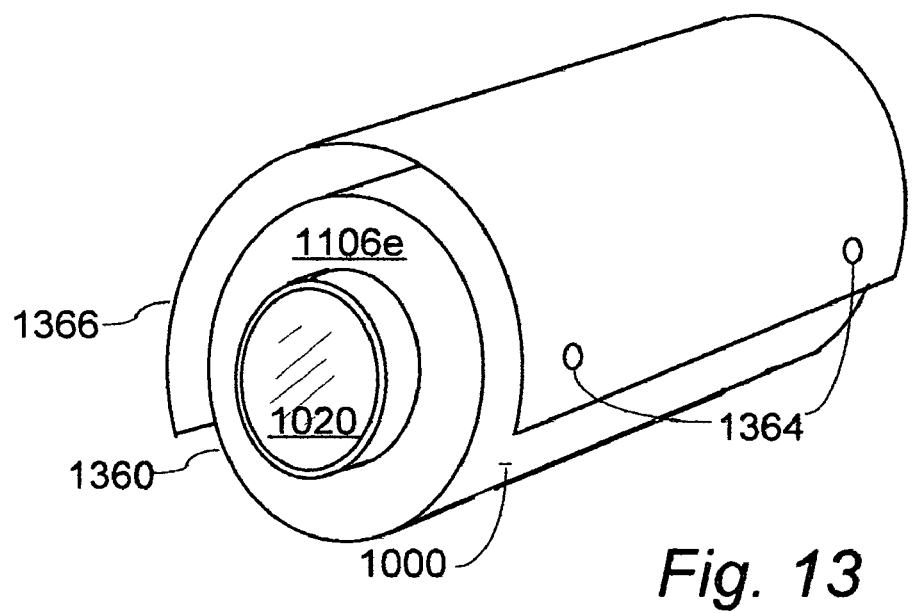
FIGS. 13 and 13a are each a pictorial representation of an alternate example of a bi-spectral selector assembly for use in combination with an infrared camera in the gas imaging system as depicted in FIG. 1.
Figure 13A:
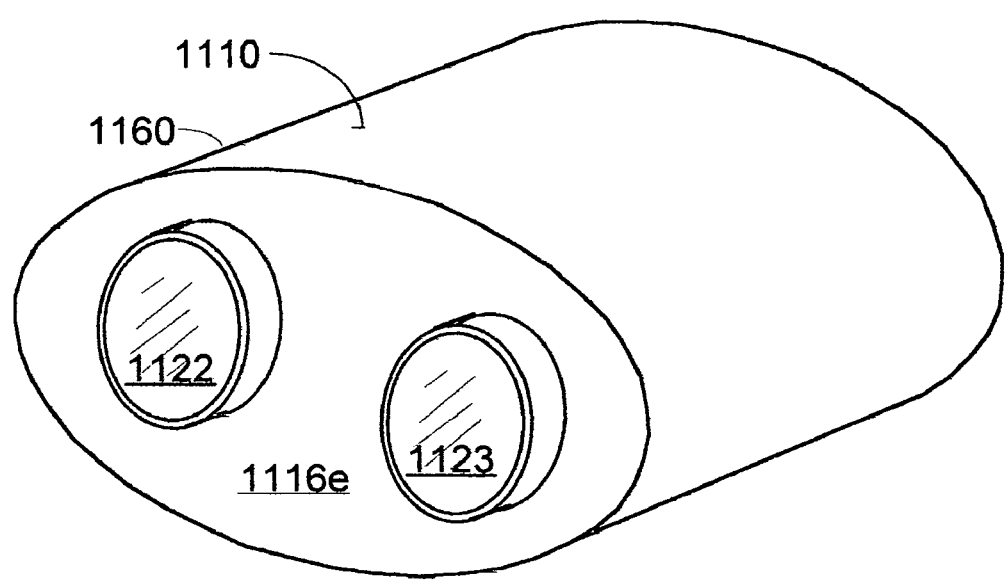

Containment structures for housing the elements of the bi-spectral assembly as thus far described particularly in relation to FIGS. 3 through 8a are representative of prototype developments. It is envisaged that a more conveniently manufacturable and more functional bi-spectral assembly unit is generally similar in appearance to that shown in FIGS. 13 and 13a. FIG. 13 is a somewhat simplified drawing showing a vessel 1000 which provides a housing for components of the bi-spectral assembly, which in this example are mounted upon an internal base plate (not visible), similar in function to the base plate 340, previously shown. The vessel 1000 includes a side wall 1360 which is illustrated as being cylindrical. The side wall 1360 is terminated at an end wall 1106e and an opposite end wall 1106f (not visible) which define the interior of the vessel 1000. The end wall 1106e carries an optical port 1020 similar to the assembly 20, previously shown. Likewise the end wall 1106f carries an optical port 1021 (not visible) and similar to the assembly 21, previously shown. In FIG. 13a, a somewhat simplified drawing shows a vessel 1100 which provides a housing for components of a stereoscopic assembly, which in this example are mounted upon an internal base plate (not visible), similar in function to the base plate 340, previously shown. The vessel 1110 includes a side wall 1160 which is illustrated as being in the form of an elliptical cylinder. The side wall 1160 extends between an end wall 1116e and an opposite end wall 1116f (not visible). These define the interior of the vessel 1110. The end wall 1116e carries an optical ports 1122 and 1123 which provide for 2 collimated beams of electromagnetic energy which impinge upon reference and absorption filters (not visible). Likewise the end wall 1116f carries a pair of optical ports (not visible). Any energies traversing the filters may be directed as reference and absorption beams, via the pair of optical ports to either a stereoscopic infrared camera or a pair of monocular infrared cameras. In another example a mirror assembly is used to direct the beams via a monocular exit port to provide an exposure similar to that illustrated in FIG. 2. The vessels shown in FIGS. 13 and 13a each provide an internal atmosphere which is at least somewhat isolated from the surrounding environment. A sealed artificial atmosphere such as dry nitrogen for example enhances the performance of the imaging system. In FIG. 13, a sun shade 1366 preferably of a reflective finish is mounted to and spaced from the wall 1360, by standoff fasteners 1364, only 2 of which are visible. The vessel in FIG. 13a may also carry a sun shade. In this particular example it is envisaged that a TE or Peltier cooler is incorporated in the side wall of either vessel such that in operation heat is transferred from inside the vessel to the external surroundings It will be evident to those of skill, that the gas imaging techniques, herein before described, are not limited to germanium glass optics for passing the mid-wavelength or long-wavelength IR. With optics of appropriate materials these techniques are also applicable for detecting gases having absorption wavelength characteristics, for example, in the visible or UV spectrums. Furthermore other embodiments of the gas imaging technique, within the scope of the appended claims, will be apparent to those of skill in this and related arts, in view of the forgoing description.

What is claimed is:

1. A gas imaging system for imaging a scene of interest which may include a plume of a gas, the imaging of the plume being dependent upon an electromagnetic wavelength absorption characteristic of the gas, the gas imaging system comprising:

a bi-spectral selector assembly for providing separate first and second paths for transmittal of electromagnetic energies emanating from the scene of interest;

a first narrow band pass filter in the first path for passing electromagnetic energy of a first wavelength corresponding to an electromagnetic wavelength absorption characteristic of said gas to the substantial exclusion of other electromagnetic energy;

a second narrow bend pass filter in the second path for passing electromagnetic energy of a second wavelength in proximity of the first wavelength and to the substantial exclusion of electromagnetic energy passed by the first narrow band pass filter;

an illuminating device for flooding the scene of interest with electromagnetic energy of wavelengths corresponding to at least the pass band wavelengths of the first and second narrow pass band filters;

an imager for capturing first and second image data of the scene of interest as represented by electromagnetic energies having traversed the first and second narrow band filters respectively, and, a processor in data communication with the imager for correlating and processing the first and the second image data, and in dependence thereupon providing displayable data including an indication of said plume of gas.

2. A gas imaging system as defined in claim 1 wherein the bi-spectral selector assembly further comprising a cavity defined by base, top, side arid end walls, ingress and egress lens assemblies mounted in the end wails and in optical communication via the separate first and second paths for transmittal of electromagnetic energies emanating from the scene of interest; and a sun shade carried spaced adjacent the top and side walls, whereby in normal use the top and side walls of the vessel are substantially shaded from any incident sunlight.

3. A gas imaging system as defined in claim 1 wherein the bi-spectral selector assembly is contained within a vessel having an interior cavity being defined by end walls being spaced one from an other and a side wall extending between and connected with the end walls, each end wail including an optical port, one of the optical ports for receiving electromagnetic energies emanating from the scene of interest and the other of the optical ports for coupling any electromagnetic energies having traversed the first and second narrow band pass filters to the imager the sun shade comprising an auxiliary wall spaced adjacent a portion of the side wall, whereby in normal use at least the portion of the side wail of the vessel is substantially shaded from any incident sunlight. the base plate being carried by the side wall.

4. A gas imaging system as defined in claim 3 further comprising a base plate carrying the bi-spectral selector and the first and second narrow band pass filters, the base plate being carried by the side wall.

5. A gas imaging system as defined in claim 3 wherein the side wall includes right and left side walls joining top and base walls, the gas imaging system further comprising a heat transfer element external of the cavity and in thermal contact with the narrow band pass filters.

6. A gas imaging system as defined in claim 3 wherein the side wall includes right and left side walls joining top and base walls, the gas imaging system further comprising a base plate carrying the bi-spectral selector and the first and second narrow band pass filters, the base plate being carried by the base wall, and a heat transfer element external of the cavity being in thermal contact with the base plate.

7. A method for imaging a scene in which there may be a plume of a fugitive gas of interest comprising the steps of:

m) capturing first and second pixel image data representative of the scene via first and second filters having narrow mutually exclusive pass bands in close proximity one with respect to the other, the pass band of the first filter being centred on a wavelength corresponding to an absorption wavelength of the gas of interest;

n) transmitting the first and second pixel image data to a processor; and o) deriving a difference pixel image partial frame by a subtraction of a fractional area of the second pixel image data from a corresponding fractional area the first pixel image data; and, p) correlating the difference pixel image partial frame with one of either the second pixel image data and a visable spectrum pixel image data representative of the scene to generate a composite frame;

whereby in a visual display of the composite frame a significant plume of the fugitive gas is identifiable and localized with respect to the scene.

8. A method as defined in claim 7 wherein the step of correlating includes the step of superimposing the lesser pixel luminance on a pixel by pixel basis.

9. A gas imaging system for imagining a scene of interest which may include a plume of a gas, the imaging of the plume being dependent upon an electromagnetic wavelength absorption characteristic of the gas, the gas imaging system comprising:

a bi-spectral selector assembly for providing separate first and second paths for transmittal of electromagnetic energies emanating from the scene of interest;

a first narrow band pass filter in the first path for passing electromagnetic energy of a first wavelength corresponding to an electromagnetic wavelength absorption characteristic of said gas to the substantial exclusion of other electromagnetic energy;

a second narrow band pass filter in the second path for passing electromagnetic energy of a second wavelength in proximity of the first wavelength and to the substantial exclusion of electromagnetic energy passed by the first narrow band pass filter;

an imager for capturing first and second image data of the scene of interest as represented by electromagnetic energies having traversed the first and second narrow band filters respectively, a processor in data communication with the imager for correlating and processing the first and the second image data, and in dependence thereupon providing displayable data including an indication of said plume of gas;

the bi-spectral selector assembly being contained within a vessel having an interior cavity being defined by end walls being spaced one from an other and a side wall extending between and connected with the end walls, each end wall including an optical port, one of the optical ports for receiving electromagnetic energies emanating from the scene of interest and the other of the optical ports for coupling any electromagnetic energies having traversed the first and second narrow band filters to the imager, and the vessel further comprising a thermal impedance material extending along surfaces of the walls of the cavity.

10. A gas imaging system as defined in claim 9 further comprising a base plate carrying the bi-spectral selector and the first and second narrow band pass filters, the base plate being carried by the side wall.

11. A gas imaging system as defined in claim 9 wherein the side wall includes right and left side walls joining top and base walls, the gas imaging system further comprising a heat transfer element external of the cavity and being in thermal contact with the narrow band pass filters.

12. A gas imaging system as defined in claim 9 wherein the side wall includes right and left side walls joining top and base walls, the gas imaging system further comprising a base plate carrying the bi-spectral selector and the first and second narrow band pass filters, the base plate being carried by the base wall, and a heat transfer element external of the cavity, the heat transfer element being in thermal contact with the base plate.

13. A gas imaging system for imaging a scene of interest which may include a plume of a gas, the imaging of the plume being dependent upon an electromagnetic wavelength absorption characteristic of the gas, the gas imaging system comprising:

a bi-spectral selector assembly for providing separate first and second paths for transmittal of electromagnetic energies emanating from the scene of interest;

a first narrow band pass filter in the first path for passing electromagnetic energy of a first wavelength corresponding to an electromagnetic wavelength absorption characteristic of said gas to the substantial exclusion of other electromagnetic energy;

a second narrow band pass filter in the second path for passing electromagnetic energy of a second wavelength in proximity of the first wavelength and to the substantial exclusion of electromagnetic energy passed by the first narrow band pass filter;

an imager for capturing first and second image data of the scene of interest as represented by electromagnetic energies having traversed the first and second narrow band filters respectively, a processor in data communication with the imager for correlating and processing the first and the second image data. and in dependence thereupon providing displayable data including an indication of said plume of gas;

wherein the bi-spectral selector assembly is contained within a vessel having an interior cavity being defined by end walls spaced one from an other and a side wall extending between and connected with the end walls, each end wall including an optical port, one of the optical ports for receiving electromagnetic energies emanating from the scene of interest and the other of the optical ports for coupling any electromagnetic energies having traversed the first and second narrow band filters as reference and absorbtion beams, to the imager, a first aperture plate for limiting cross sectional dimensions of reference and absorption transmission paths, and a thermal impedance material extending along surfaces of the walls of the cavity.

14. A gas imaging system as defined in claim 13 further comprising a base plate carrying the bi-spectral selector and the first and second narrow band pass filters, the base plate being carried by the side wall.

15. A gas imaging system as defined in claim 13 wherein the side wall includes right and left side walls joining top and base walls, the gas imaging system further comprising a heat transfer element external of the cavity, the heat transfer element being in thermal contact with the narrow band pass filters.

16. A gas imaging system as defined in claim 13 wherein the side wall includes right and left side walls joining top and base walls, the gas imaging system further comprising a base plate carrying the bi-spectral selector and the first and second narrow band pass filters, the base plate being carried by the base wall, and a heat transfer element external of the cavity, the heat transfer element being in thermal contact with the base plate. material extending along surfaces of the walls of the cavity.

17. A gas imaging system for imaging a scene of interest which may include a plume of a gas, the imaging of the plume being dependent upon an electromagnetic wavelength absorption characteristic of the gas, the gas imaging system comprising:

a bi-spectral selector assembly for providing separate first and second paths for transmittal of electromagnetic energies emanating from the scene of interest;

a first narrow band pass filter in the first path for passing electromagnetic energy of a first wavelength corresponding to an electromagnetic wavelength absorption characteristic of said gas to the substantial exclusion of other electromagnetic energy;

a second narrow band pass filter in the second oath for passing electromagnetic energy of a second wavelength in proximity of the first wavelength and to the substantial exclusion of electromagnetic energy passed by the first narrow band pass filter;

an imager for capturing first and second image data of the scene of interest as represented by electromagnetic energies having traversed the first and second narrow band filters respectively;

a processor in data communication with the imager for correlating and processing the first and the second image data, and in dependence thereupon providing displayable data including an indication of said plume of gas;

a heat transfer element in thermal contact with the narrow band pass filters, whereby the narrow band pass filters are maintained at a temperature substantially no greater than an atmospheric ambient temperature.

18. A gas imaging system as defined in claim 17 further comprising a base plate carrying the bi-spectral selector and the first and second narrow band pass filters, and wherein the heat transfer element is external of the cavity and in thermal contact with the base plate.

* * * * *